United States Patent
Higgins

(10) Patent No.: US 7,319,894 B2
(45) Date of Patent: *Jan. 15, 2008

(54) CONTINUOUS SPECTROSCOPIC MEASUREMENT OF TOTAL HEMOGLOBIN

(75) Inventor: Michael J. Higgins, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/521,324

(22) Filed: Sep. 13, 2006

(65) Prior Publication Data

US 2007/0060810 A1 Mar. 15, 2007

Related U.S. Application Data

(60) Provisional application No. 60/716,695, filed on Sep. 13, 2005.

(51) Int. Cl.
*A61B 5/00* (2006.01)

(52) U.S. Cl. ...................................... 600/328; 600/322

(58) Field of Classification Search ................ 600/320, 600/322, 323, 328
See application file for complete search history.

(56) References Cited

U.S. PATENT DOCUMENTS

| | | | | |
|---|---|---|---|---|
| 5,755,226 A | * | 5/1998 | Carim et al. ................ 600/323 |
| 5,782,756 A | * | 7/1998 | Mannheimer ................ 600/322 |
| 5,830,133 A | * | 11/1998 | Osten et al. ................ 600/322 |
| 6,049,727 A | * | 4/2000 | Crothall ...................... 600/310 |
| 6,064,474 A | | 5/2000 | Lee et al. |
| 6,103,197 A | | 8/2000 | Werner |
| 6,473,632 B1 | | 10/2002 | Myers |
| 2002/0016536 A1 | * | 2/2002 | Benni ......................... 600/323 |
| 2003/0009090 A1 | | 1/2003 | Jeon et al. |
| 2003/0123047 A1 | | 7/2003 | Petterson et al. |
| 2003/0139667 A1 | * | 7/2003 | Hewko et al. .............. 600/410 |

* cited by examiner

*Primary Examiner*—Eric Winakur
*Assistant Examiner*—Etsub D Berhanu
(74) *Attorney, Agent, or Firm*—Gregory J. Carlin; Rajiv Yadav; David Hauser

(57) ABSTRACT

Methods for measuring the total hemoglobin of whole blood include measuring reflective light at multiple wavelengths within the visible spectrum, calculating light absorbance at each of the multiple wavelengths, performing a comparison in a change in like absorbance between the multiple wavelengths, and/or relating the comparison to total hemoglobin. A system for measuring total hemoglobin of whole blood may include at least one light source, a catheter, optical fibers, at least one photodetector, data processing circuitry, and/or a display unit.

15 Claims, 11 Drawing Sheets

----- White LED Spectrum

CONTINUOUS SPECTROSCOPIC MEASUREMENT OF TOTAL HEMOGLOBIN

CLAIM OF PRIORITY UNDER 35 U.S.C. § 119

The present application claims priority to U.S. Provisional Patent Application No. 60/716,695, filed Sep. 13, 2005, entitled "Spectroscopic Method for Continuous Intravascular Measurement of Total Hemoglobin in Whole Blood," and assigned to the assignee hereof and hereby expressly incorporated by reference herein.

BACKGROUND OF THE INVENTION

The present disclosure relates to the measurement of total hemoglobin (tHb) of whole blood. The tHb is commonly measured, either directly or indirectly, using a variety of diagnostic systems and methods. Healthy tHb levels in patients encourage proper biological function within those patients. When tHb levels are within normal ranges, the hemoglobin within red blood cells delivers adequate oxygen from the lungs to the body's tissues and returns appropriate levels of carbon dioxide from the tissues to the lungs.

Patients having abnormal tHb or abnormal levels of tHb suffering from various conditions including anemia, sickle cell anemia, loss of blood, nutritional deficiency, bone marrow problems and disorders, including polycythemia rubra vera, dehydration, lung disease, certain tumors, and drug abuse, including abuse of the drug erythropoietin. The accurate and efficient measurement of tHb can be a very common and helpful diagnostic procedure in detecting and managing such conditions.

The tHb is measured using a variety of tests, most of which are performed in a hospital or laboratory using expensive laboratory measurement equipment or invasive techniques of varying accuracy. For example, blood may be drawn from a patient, and the red blood cells are later broken down and the hemoglobin is formed into a solution. The free hemoglobin is then exposed to a chemical containing cyanide, which binds tightly with the hemoglobin molecule to form cyanmethemoglobin. After bonding, light is shined through the solution, and the total amount of light absorbed by the solution is measured at a typical wavelength of 540 nanometers (nm). Based upon the total amount of light absorbed by the solution, the tHb is determined using the Lambert-Beer law.

Various other non-invasive and invasive tHb measurement procedures may be employed. Few, if any, provide maximum accuracy, efficiency, and convenience to patients and healthcare professionals. Therefore, a need exists for systems and methods that increase the accuracy, efficiency, and convenience of tHb measurements for patients.

SUMMARY OF THE INVENTION

The present invention has been developed in response to problems and needs in the art that have not yet been fully resolved by currently available tHb measurement systems, devices, and methods. Thus, these developed systems, devices, and methods provide ways of spectroscopically measuring the tHb of whole blood in a minimally invasive, accurate, and continuous manner.

Various advantages of the devices, systems, and/or methods described herein are provided over previous devices, systems, and/or methods of the prior art. For example, one advantage may include a continuous form of accurate measurement. Currently, there appears to be no reliable and minimally-invasive method of placing an indwelling probe inside the blood stream or in a solution of whole blood to measure tHb continuously. Another advantage may include a continuous measurement that allows changes in tHb to be presented to a user for timely action. The user may act upon the information faster than waiting until a blood sample is drawn and the results are returned to the user. The user has the benefit of understanding the immediate state of a patient at any time rather than only at the time the sample was drawn and tested. Such contemporaneous and simultaneous measurement may provide critical information at a time when it is most needed.

Another advantage may include using reflectance spectroscopy to allow for a probe to be placed within a blood vessel. However, the methods contemplated herein do not require placement within a blood vessel, rather a probe or other measurement instrument may be used to measure whole blood intravascularly or extravascularly. In the embodiment where a probe is used intravascularly, there may not be a need for an extracorporeal circuit such as the devices currently used for hemodialysis monitoring.

A method of measuring total hemoglobin of whole blood may include measuring reflected light at multiple wavelengths in the visible spectrum, calculating light absorbance at each of the multiple wavelengths, performing a comparison in a change in light absorbance between the multiple wavelengths, and/or relating the comparison to total hemoglobin. Calculating light absorbance at each of the multiple wavelengths may include calculating light absorbance based upon multiple measurements of reflected light at each of the multiple wavelengths. The method may also include relating total hemoglobin to hematocrit.

In embodiments where reflectance spectroscopy is used, another advantage may include employing the spectra of a white light emitting diode (LED) as the illuminating light source used with the systems and methods described herein. The spectral output of a white LED is about 500 nm to 900 nm, which advantageously peaks at about 550 nm. Since blood oxygen absorbance also peaks at about 550 nm, use of a white LED will likely yield a superior data reading. Further, since the spectral output range of a single white LED is sufficiently broad to provide reliable oxygen absorbance readings using reflectance spectroscopy, multiple light sources may not be used, decreasing the cost and improving reliability of the system.

While a single white LED with a broad spectral range may be preferred, multiple light sources, including multiple colored LEDs covering multiple narrow, discrete spectral ranges may be employed. Multiple LEDs often require calibration at the time of use in order to assure accurate measurement. However, a single LED would not require such calibration since the light from such LED will not be inconsistent with any second light source. Yet, multiple color LEDs may be combined, constantly calibrated as needed, and time multiplexed to provide an alternate form of measuring tHb.

Another light source may include an incandescent lamp, such as a tungsten halogen lamp, which generates infrared (IR) light. Such light sources are relatively expensive and generate heat from the IR light, which heat may distort the accuracy of tHb readings if not corrected using the systems and methods described herein.

Other advantages may include using a standard fiber-optic catheter that is normally used and manufactured for routine oxygen saturation measurements. Another advantage may include oxygen saturation and hematocrit that can be measured with the same spectrometer. Any of the above advantages may be taken in any combination with various other advantages not discussed herein in order to yield the devices, systems, and methods as claimed.

The multiple wavelengths may include two different wavelengths such as a first wavelength and a second wavelength. The first wavelength may yield less change in light absorbance than the second wavelength as a result of performing a comparison in a change in light absorbance between the multiple wavelengths. The first wavelength may be, for example, about 625-850 nm, such as about 700-720 nm or about 805 nm. The second wavelength may, for example, be within the range of about 500-600 nm or about 540-560 nm, such as about 548 nm.

A method of measuring total hemoglobin of whole blood may include providing a light source, measuring a reference signal containing the spectra of the light source, turning the light source off and measuring a dark signal, turning the light source on and measuring a total hemoglobin remitted spectra from whole blood, verifying that the signal levels of the remitted spectra are within a preferred range, removing dark spectra from the remitted spectra, calculating light absorbance from the reference signal and the remitted signal, and/or calculating the difference in light absorbance between multiple wavelengths. The method may also include removing noise from the reference signal and the remitted signal before calculating light absorbance from the reference signal and the remitted signal. The method may also include correcting for any stray light from the light source.

The method may also include calculating an n-point average about one of the multiple wavelengths. At least one of the multiple wavelengths may be less than about 750 nm in the visible light spectrum, and the method may also include correcting for light absorbance error of the at least one multiple wavelength due to the effect of oxygen saturation. The method may also include converting the difference in light absorbance between multiple wavelengths to total hemoglobin concentration.

Yet another method of measuring total hemoglobin may include a method of spectroscopically and continuously measuring total hemoglobin of whole blood. This method may include any of the following steps taken in any combination: providing a spectroscope in communication with whole blood, measuring a reference signal containing the spectra of the spectroscope, turning the spectroscope off and measuring a dark signal from the whole blood, turning the spectroscope on and measuring a total hemoglobin remitted spectra from the whole blood, verifying that signal levels of the remitted spectra are within a preferred range, removing dark spectra from the remitted spectra, calculating light absorbance from the reference signal and the remitted signal, and/or calculating the difference in light absorbance between multiple wavelengths.

The method may also include removing noise from the reference signal and the remitted signal before calculating light absorbance from the reference signal and the remitted signal. The method may also include calculating an n-point average about one of the multiple wavelengths. At least one of the multiple wavelengths may be less than about 750 nm within the visible light spectrum, and the method may also include correcting for light absorbance error of the at least one multiple wavelength due to the effect of oxygen saturation. The method may also include converting the difference in light absorbance between multiple wavelengths to total hemoglobin concentration, and/or correcting for stray light from the light source.

An apparatus for measuring total hemoglobin of whole blood may include at least one light source, a catheter in communication with the at least one light source, a transmit optical fiber in communication with the at least one light source, a receive optical fiber in communicable proximity to the transmit optical fiber, at least one photodetector in communication with the receive optical fiber, data processing circuitry in communication with the at least one photodetector, and/or a display in communication with the data processing circuitry. The transmit optical fiber and the receive optical fiber may be secured to the catheter. For example, the transmit optical fiber and the receive optical fiber may be housed within the catheter.

The at least one light source may include a single light source that emits multiple wavelengths. The at least one photodetector may include multiple photodetectors that multiplex the multiple wavelengths from the single light source. And, the single light source may include a white light emitting diode.

The at least one light source may include multiple light sources that each emit a discrete wavelength. The system may also include sequencer control logic, and the sequencer control logic may time multiplex the multiple light sources to provide that only one multiple light source emits light at a time. The system may also include a wavelength filter, and the wavelength filter may filter the multiple light sources to provide that only a single discrete wavelength passes through the filter at a time. The multiple light sources may include color light emitting diodes and/or an incandescent lamp, such as a tungsten halogen lamp.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE DRAWINGS

In order that the manner in which the above-recited and other features and advantages of the present invention are obtained is readily understood, a more particular description of the present invention briefly described above will be rendered by reference to specific embodiments thereof which are illustrated in the appended drawings. These drawings depict only typical embodiments of the present invention and are not therefore to be considered to limit the scope of the present invention.

DETAILED DESCRIPTION

Figure 1:
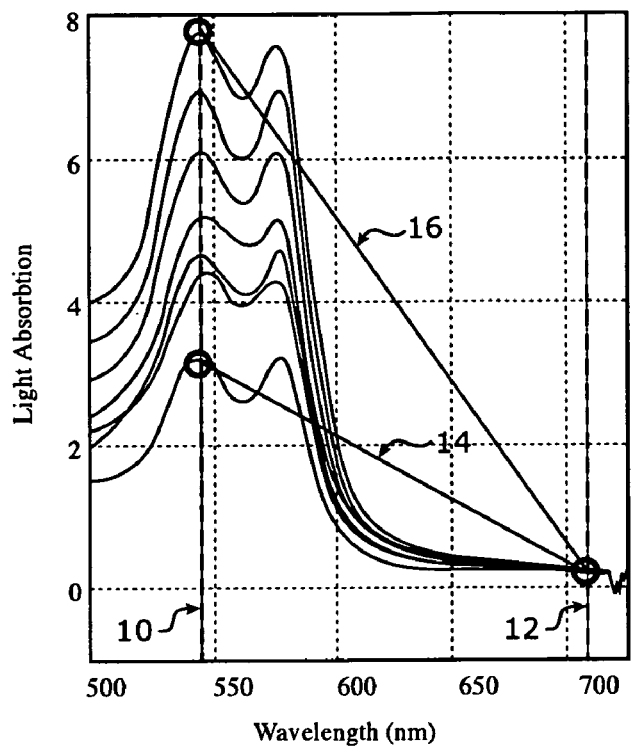
FIG. 1 is a chart illustrating the change in absorbance of light at various wavelengths for different amounts of total hemoglobin.

Claimed subject matter is particularly pointed out and distinctly claimed in the concluding portion of the specification. However, such subject matter may be understood by reference to the following detailed description when read with the accompanying figures. Thus, the following detailed description, as represented in the figures, is not intended to limit the scope of the present invention as claimed, but is merely representative of embodiments of the present invention.

A spectroscopic reference method for continuously measuring the total hemoglobin (tHb) of whole blood may include the use of any spectroscope or other device, such as a fiber optic catheter, in communication with whole blood. For example, the fiber optic catheter may be placed intravascularly. The measurement method uses differential absorbance spectroscopy combined with reflectance spectroscopy to calculate tHb. The various methods described herein measure tHb content. However, hematocrit (Hct) and tHb may be used interchangeably. The relationship between Hct and tHb is as follows:

$$tHb\left(\frac{g}{dL}\right) = 0.33 * Hct(\%)$$

Certain methods of measuring tHb may be used. For example, many commercial tHb measurements are made in the laboratory or using laboratory instruments. To measure tHb, a blood sample is lysed, creating a stroma-free hemoglobin solution that is chemically converted mole-for-mole to a more stable and measurable hemiglobincyanide (HiCN) by adding an HiCN reagent. The HiCN concentration is determined by measuring the sample absorbance at 540 nanometers (nm) and at a known pathway length, typically 1 centimeter (cm). The millimolar (mmol) extinction coefficient of HiCN at 540 nm is 11.0 Liters $*mmol^{-1}*cm^{-1}$. The concentration of tHb (ctHb) at 540 nm can be calculated according to the Lambert-Beer law, as follows:

$$c_{tHb} = \frac{A_{540\,nm}^{HiCN}}{\varepsilon_{540\,nm}^{HiCN} * L}$$

where A is the absorptivity to light of the solution, $\epsilon$ is the millimolar extinction coefficient and L is the optical pathlength.

Another method for measuring tHb employs near infrared (NIR) spectroscopy for invasive and non-invasive determination of Hct. These methods use multiple light-emitting diodes (LEDs) to emit discrete wavelengths in the NIR spectrum. Operating in the NIR spectrum requires the use of light detectors that have sufficient sensitivity within this region of the spectrum. Such operation must also account for light absorbance by water, since water has significant spectral features within the NIR spectrum.

Another method of measuring tHb employs the use of intravascular probes using multiple optical fibers. One optical fiber transmits light into the blood stream while two fibers receive the reflected signal from the blood stream. The optical fibers are located at the distal end of the probe or catheter of the intravascular probe such that the two receiving fibers are positioned at different distances from the transmitting fiber. The different distances create a difference in pathlength. An isobestic wavelength is communicated through the fibers since such a wavelength is insensitive to oxygen saturation within the bloodstream. The ratio of reflected light signals at the wavelength is a function of the concentration of absorbing particles within the effective pathlength between the transmitting fiber and the two receiving fibers. This method may use at least three optical channels within the probe or catheter. Various improvements upon the methods described above are both preferred and possible, and will be described below.

Referring to FIG. 1, a method of calculating tHb within whole blood is based on the concept of differential absorbance between multiple wavelength points. In general, using at least two points is desirable. However, any number of points may be used in order to provide a desired method for measuring tHb or any point that is insensitive to changes in oxygen saturation ($SO_2$) and tHb. Where at least two points are used, a point 10 and a point 12 may be used. The point 10 may change significantly to a change in Hct and may be isosbestic with respect to oxygen saturation. The point 12 may change insignificantly to a change in Hct, rendering point 12 effectively isosbestic with respect to tHb and oxygen saturation, even though point 12 is not a true isosbestic point as shown in FIG. 1. In practice, the point 12 which responds insignificantly to Hct changes does not necessarily need to be an isosbestic point. Rather, the point 12 can be any wavelength that is insensitive to Hct changes. Such wavelengths are wavelengths where the millimolar extinction coefficients are small.

As tHb increases, the amount of light absorbance increases significantly for point 10 and insignificantly, if at all, for point 12. As a result of the increase in tHb and light absorbance, the slope of the line 14 changes to the slope of the line 16. The slope for both lines 14 and 16 is calculated by taking the difference in absorbance (dA) divided by the difference in wavelength (dλ), where dλ is about 700 nm less about 548 nm. The slope of line 14 indicates a lower amount of tHb, and the steeper slope of line 16 indicates a higher amount of tHb.

As shown in FIG. 1, the point 10 which is sensitive to a change in absorbance due to tHb is, for example, at a wavelength of about 548 nm. The point 12 that is relatively insensitive to changes in oxygen saturation and tHb is, for example, at a wavelength between about 700 nm and about 750 nm. Either of the points 10 and 12 may be set by a user of the methods described herein to any useful wavelength within the visible light spectrum.

Figure 2:
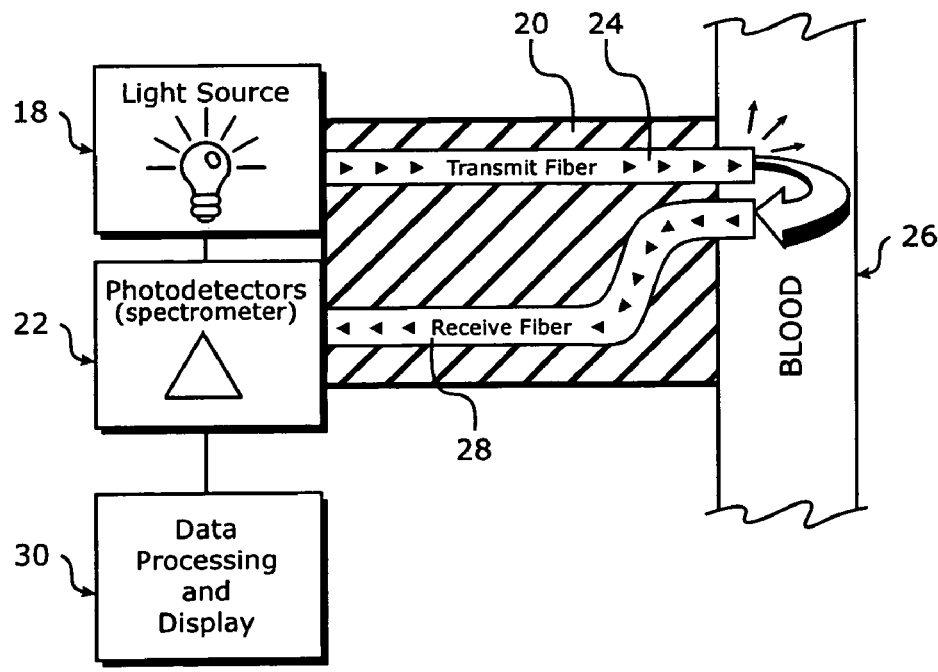
FIG. 2 is a schematic representation of components that may be employed to measure total hemoglobin.

Referring to FIG. 2, the apparatus used to measure tHb may include a light source 18, such as a white LED, a catheter 20, and a spectrometer 22. The apparatus may also includes data processing circuitry and a display 30 capable of providing users of the apparatus with a means to control and view the processes and results of the methods performed by the apparatus. The light source 18 transfers light through a transmit optical fiber 24 into blood 26, illuminating the blood 26 with light in a wavelength range of between about 400 nm to about 750 nm. The blood 26 may be blood flowing intravascularly within a patient or may be blood removed from a patient and analyzed, for example, in a hospital, laboratory, or similar setting. The catheter 20 may be a central venous catheter, which may include two parallel optical fibers. In an embodiment, the first parallel optical fiber is a transmit fiber 24 and the second parallel optical fiber is a receive fiber 28 capable of receiving reflected light from the blood and transferring the reflected light into the spectrometer 22.

The embodiment described with reference to FIG. 2 is an example of an embodiment employing discrete time with a multiplexed wavelength. That is, a single light source 18, such as a white LED, is turned on continuously over a discrete period of time. A plurality of wavelengths from the single light source is transmitted into the blood 26 and reflected back into the instrument through the receive fiber 28. The returned signal is then Fourier transformed and multiplexed, or separated into a continuous spectrum of unique wavelengths. Ranges of the unique wavelengths are measured simultaneously by multiple photodetectors of the spectrometer 22. Alternate or additional systems and methods, including those employing discrete wavelengths that are time multiplexed, may be used to measure tHb, as described with reference to FIGS. 2A and 2B, for example.

Figure 2A:
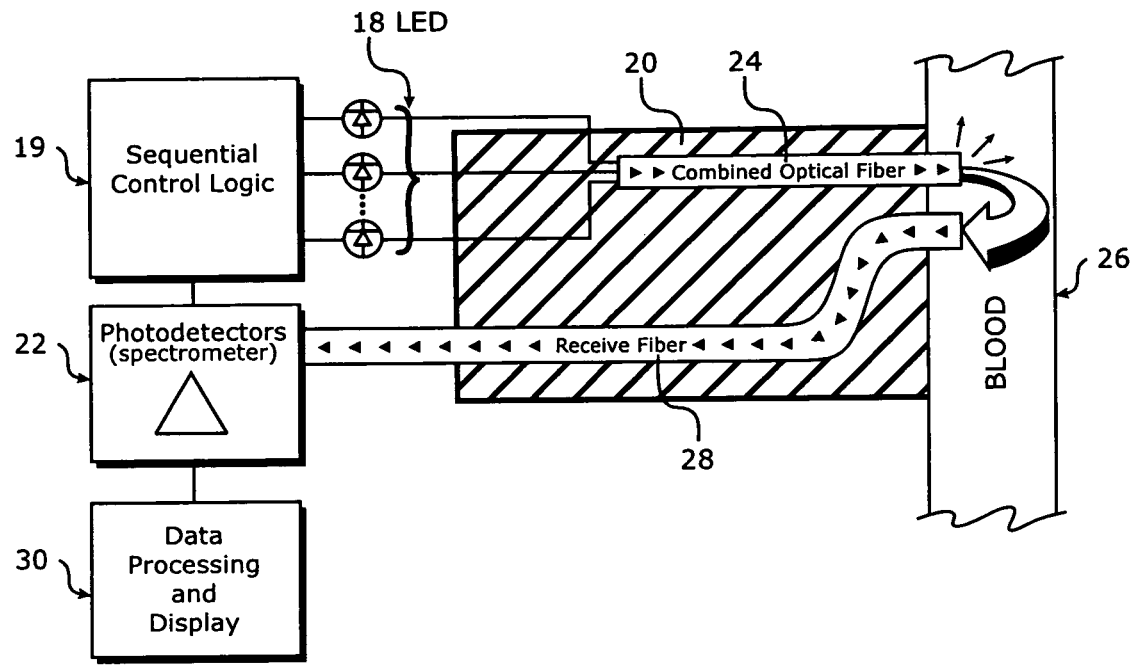
FIG. 2A is a schematic representation of another example of components that may be employed to measure total hemoglobin.

Referring to FIG. 2A, multiple light sources 18, such as multiple colored LEDs, providing discrete wavelengths may be time multiplexed by sequencer control logic 19 to individually turn on at different times. The discrete signals are transmitted through a combined optical transmit fiber 24 into the blood 26 and reflected into a receive fiber 28. The receive fiber 28 transmits the discrete reflected signals to a single photodetector of a spectrometer 22. Multiple photodetectors may be employed to measure the special effects of the signals. If more than one light source 18 is turned on at the same time, i.e., the signals are not time multiplexed, a photodetector 22 will be unable to distinguish between the multiple light sources 18 and may sum the multiple signals based on the photodetector's sensitivity to wavelength.

Figure 2B:
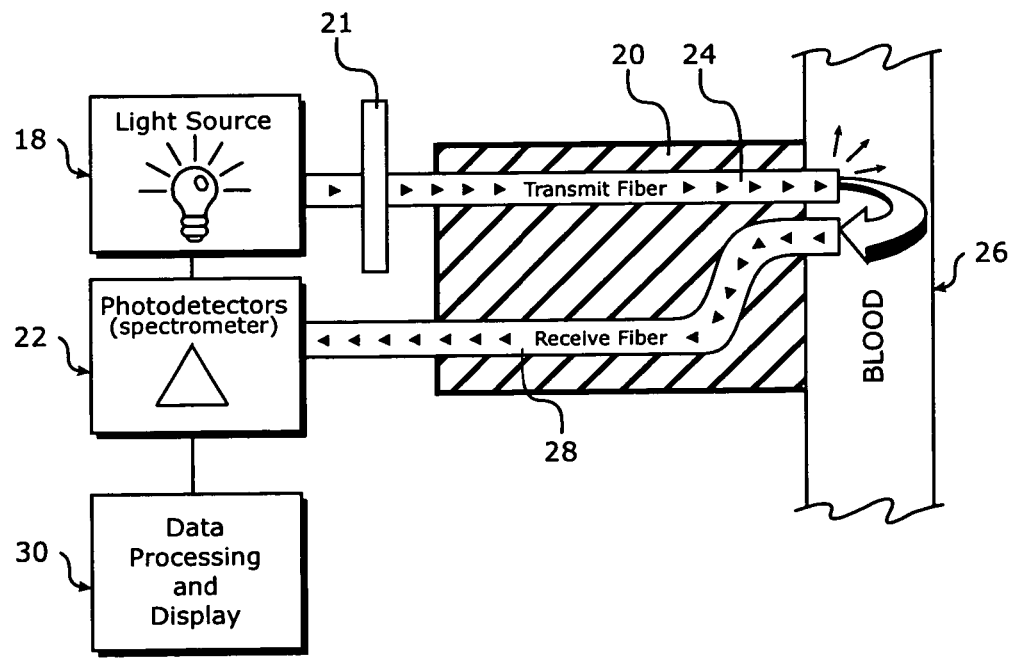
FIG. 2B is a schematic representation of yet another example of components that may be employed to measure total hemoglobin.

Referring to FIG. 2B, a single or multiple light sources 18 may be transmitted through a wavelength filter 21, such as a filter wheel, to provide an alternate or additional embodiment of discrete wavelengths that may be time multiplexed. The light signals are passed through the filter 21 and transmitted through an optical fiber 24 into blood 26 and then reflected back through a receive fiber 28 to at least one photodetector 22.

Any catheter 20 may be used, including the central venous catheter already mentioned and a pulmonary artery catheter for measuring oxygen saturation. A pulmonary artery catheter for measuring oxygen saturation also includes parallel optical fibers capable of achieving the desired results of the methods described herein. Any spectrometer may be used, however, the spectrometer 22 should preferably be capable of measuring within the range of between about 500 nm and 750 nm. The spectrometer should also have low stray light specifications in order to minimize the undesired affects of stray light that will be discussed herein.

Another example of a system of measuring tHb may include a system console, a laptop computer, an optical module, and an oximetry catheter. The system console may function as the light source that emits light that is transmitted into blood through the optical module that connects to the oximetry catheter. The light may be reflected back through the catheter 20, as previously described with reference to FIG. 2, to the system console and the spectral data collected may then be used to calculate oxygen saturation and tHb. For example, the PreSep Oximetry catheter by Edwards Lifesciences may be used with oximetry monitors to measure oxygen saturation and also provides a means to measure hemoglobin within the system.

The system may be used in patients who require monitoring of hemodynamic parameters, including oxygen saturation and hemoglobin. Monitoring of these parameters may provide a measurement by the catheter 20 of oxygen saturation and hemoglobin. Any of the following devices may be used as components of the system: the Vigilance Continuous Cardiac Output/Oximetry/Continuous End Diastolic Volume Monitor; the CDI Blood Parameter Monitoring System 500 by 3M; a central venous oximetry probe catheter and probe; the Multi-Med Multi-Lumen Central Venous Catheter; and/or the Edslab Dual Lumen Regional Saturation Oximetry Catheter.

Figure 3:
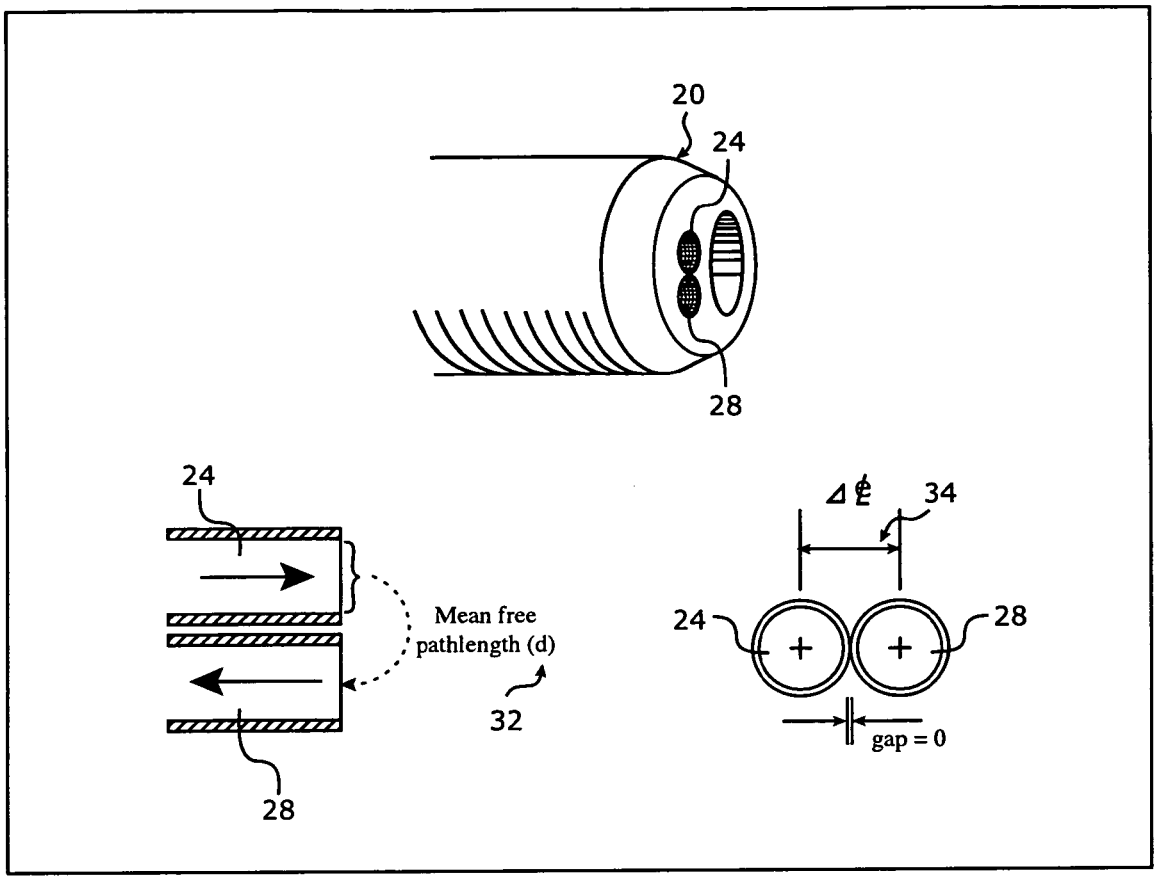
FIG. 3 illustrates the tip of a catheter and the pathlength within two optical fibers exposed at the end of the catheter.

Referring to FIG. 3, tHb concentration is also dependent upon a pathlength d 32. The pathlength d 32 is a mean free pathlength between a core of the transmit fiber 24 and a core of the receive fiber 28. The pathlength d 32 is controlled by the geometry of the optical fibers 24 and 28 at the tip of the catheter 20. The core-to-core spacing 34 is the primary parameter that affects the optical pathlength d 32. Since the parameter of the distance or spacing from both cores of the fibers 24 and 28 is tightly controlled within the catheter 20 fabrication process, pathlength d 32 can be considered constant. Variability due to small changes in pathlength d 32 can be corrected for by processing the absorbance difference through a mathematical transform, determined empirically to linearize the results.

According to the Lambert-Beer law, the output of the system and/or apparatus described with reference to FIGS. 2 and 3 is a function of the logarithm of the extinction coefficient ($\epsilon$), the concentration (c), and the pathlength (d) 32 according to the following relationship:

$$I(\lambda) = I_0(\lambda) e^{-\epsilon(\lambda) c d}$$

where the extinction coefficient $\epsilon(\lambda)$ varies as a function of the wavelength. For example, in the wavelength region of about 805 nm, the extinction coefficient is very small when compared to the extinction coefficient within a wavelength region of about 500-600 nm. Therefore, as concentration or pathlength changes, the proportional change in I is small at about 805 nm as compared to the change in I at the region of about 500-600 nm. By referencing the light absorbance at one of the wavelengths for points 10 within the about 500-600 nm wavelength range to the wavelength of point 12 at about 805 nm, a change in light absorbance due to changes in tHb concentration can be determined. The wavelength of about 805 nm is an example wavelength only and may be replaced by any other wavelength likely to give an accurate reading of tHb, such as any wavelength within the range of about 625-850 nm. For example, a wavelength of about 700 nm would also be effective since the difference in light absorbance between about 700 nm and about 805 nm is very small when compared to the light absorbance within the range of about 500-600 nm.

Figure 4:
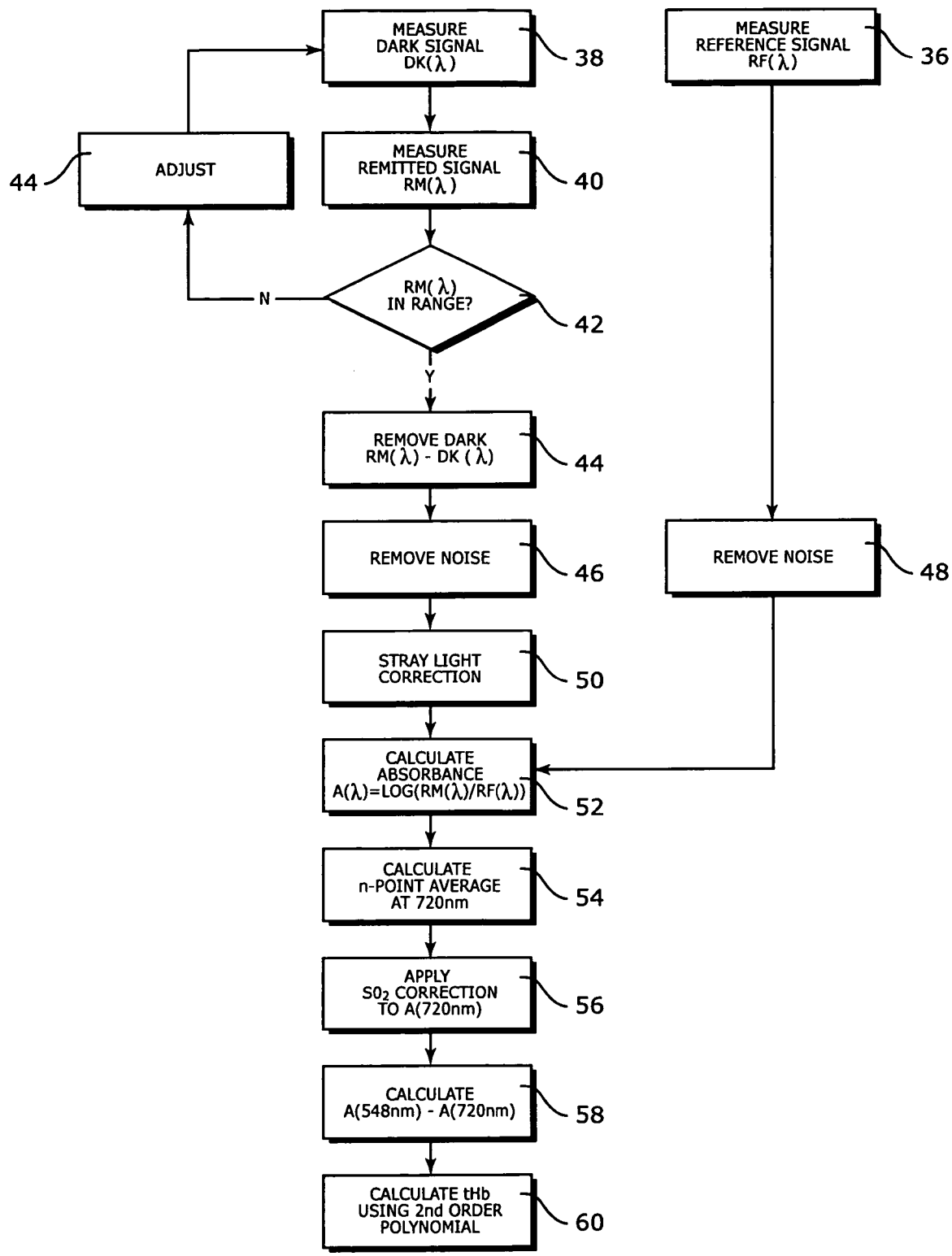
FIG. 4 is a flow chart illustrating various steps in a method that may be employed to measure total hemoglobin.

Referring to FIG. 4, an embodiment for calculating tHb from a spectroscopic signal is shown and described. As shown in FIG. 4, a method of measuring tHb of whole blood may include a reference signal $RF(\lambda)$ containing the spectra of the light source at step 36. After measuring the reference signal at step 36, the method includes turning the light source off and measuring a dark signal $DK(\lambda)$ at step 38. Step 38 is followed by turning the light source back on and measuring the tHb remitted spectra signal $RM(\lambda)$ from the whole blood at step 40. Step 40 is followed by verifying that the remitted spectra signal $RM(\lambda)$ levels are within a preferred range at step 42. If the signal levels of the remitted spectra are not within the preferred range, an adjustment is made at step 44 so that the remitted spectra signal $RM(\lambda)$ is within the preferred range. Steps 38 through 44 may be repeated until signal levels of the remitted spectra are verified within the preferred range.

The preferred range for verified remitted spectra is most likely within the region of about 500-600 nm for point 10 and from about 625 nm up to any wavelength where the instrument used is not saturated with light, yielding unpredictable data, for point 12. Within the region of about 500-600 nm, the intensity of light units should be above 5% of the minimum light units possible. Within the wavelength region of about 625 nm and above, the intensity of light units should be below 95% of the maximum light units possible.

The dark signal $DK(\lambda)$ may alternately or additionally be removed electronically, rather than merely mathematically, to ensure that the dark signal $DK(\lambda)$ is always zero. In these embodiments, the dark signal $DK(\lambda)$ may be measured when the spectroscope is manufactured, calibrated, and/or used. Since electronic removal of the dark signal $DK(\lambda)$ will not compensate for thermal changes or ambient light effects, this alternate or additional step may be combined with other steps described herein to provide a helpful adjusted measurement.

After signal levels of the remitted spectra are within the preferred range, step 42 is followed by removing dark spectra from the remitted spectra, or subtracting $DK(\lambda)$ from $RM(\lambda)$, removing common mode noise at step 44. Step 44 may be followed by removing additional noise from the reference signal and the remitted signal by employing any type of mathematical reduction of noise, for example a noise reduction method using a moving average filter to remove noise or signals from both dark and light signals, may be employed at steps 46 and 48. Any steps described with reference to FIG. 4 may be preceded or followed by step 50, a step for correcting for stray light from the light source. Further, steps 46 and 48 may be performed at any time in relation to step 44.

In an embodiment, the method may also include the step of calculating light absorbance from the reference signal and the remitted signal at step 52. Following step 52, calculating an n-point average about at least one of the multiple wavelengths may occur at step 54. Following step 54, at least one of the wavelengths may be less than about 750 nm within the visible light spectrum for a white LED, since the optical power at a wavelength greater than about 700 nm is very small for a white LED, resulting in very low signal levels and a low signal-to-noise ratio. Such a wavelength point, for example, about 720 nm, may be prone to light absorbance error due to the effect of oxygen saturation. Thus, at step 56, the method may include correcting for light absorbance error of at least one wavelength, for example, 720 nm, due to the effect of oxygen saturation.

The method described with reference to FIG. 4 may also include calculating the difference in light absorbance between the multiple wavelengths at step 58. Following calculation at step 58, the method may also include converting the difference of light absorbance between multiple wavelengths to tHb concentration using a calculation of tHb concentration according to a second order polynomial at step 60.

Any of the steps described with reference to FIG. 4 may be performed in any order capable of providing a method of measuring tHb in whole blood. Further, in certain embodiments, not every step described with reference to FIG. 4 is required in order to achieve the method as set forth in the claims. For example, in an embodiment, step 60 may be required if the stray light correction is not applied at step 50. Further, steps 46, 48, 50, 54, and 56, are optional to the claimed method, and may be employed in order to improve the accuracy of the method results.

Figure 5:
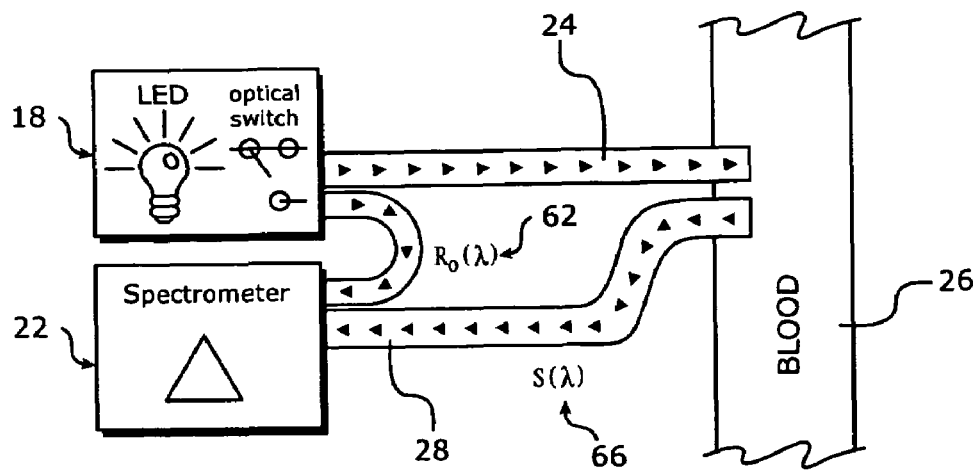
FIG. 5 is a schematic representation of step 36 of FIG. 4.

The following FIGS. 5 through 11 will provide additional detail of the steps described with reference to FIG. 4. Referring to FIG. 5, the method for determining tHb may include measuring a reference signal containing the spectra of the light source 18. Measuring the reference signal can be accomplished in a number of ways. One method is to provide an optical feedback path $R_0(\lambda)$ 62 that permits the light from the light source 18 to be sampled by the spectrometer 22 before or during each measurement. The reference signal $R_0(\lambda)$ 62 is assumed to be roughly equal to a similar signal communicated from the light source 18 through the transmit fiber 24 to the blood 26 as a reference signal $R_1(\lambda)$ 64. However, the intensity of $R_0(\lambda)$ 62 need not be the same as the intensity of $R_1(\lambda)$ 64, since both $R_0(\lambda)$ 62 and $R_1(\lambda)$ 64 will likely share the same spectral shape. The gain factor can be normalized between the similar spectral shapes for $R_0(\lambda)$ 62 and $R_1(\lambda)$ 64 to produce a helpful comparison.

The return signal is then sent through the receive fiber 28 as signal $S(\lambda)$ 66. The absorptivity, A, is equal to the logarithm of $S(\lambda)$ 66 divided by the reference signal $R_0(\lambda)$ 62. This method is relatively precise. The method may continually measure and adjust for spectral changes that may occur from the light source 18.

Figure 6:
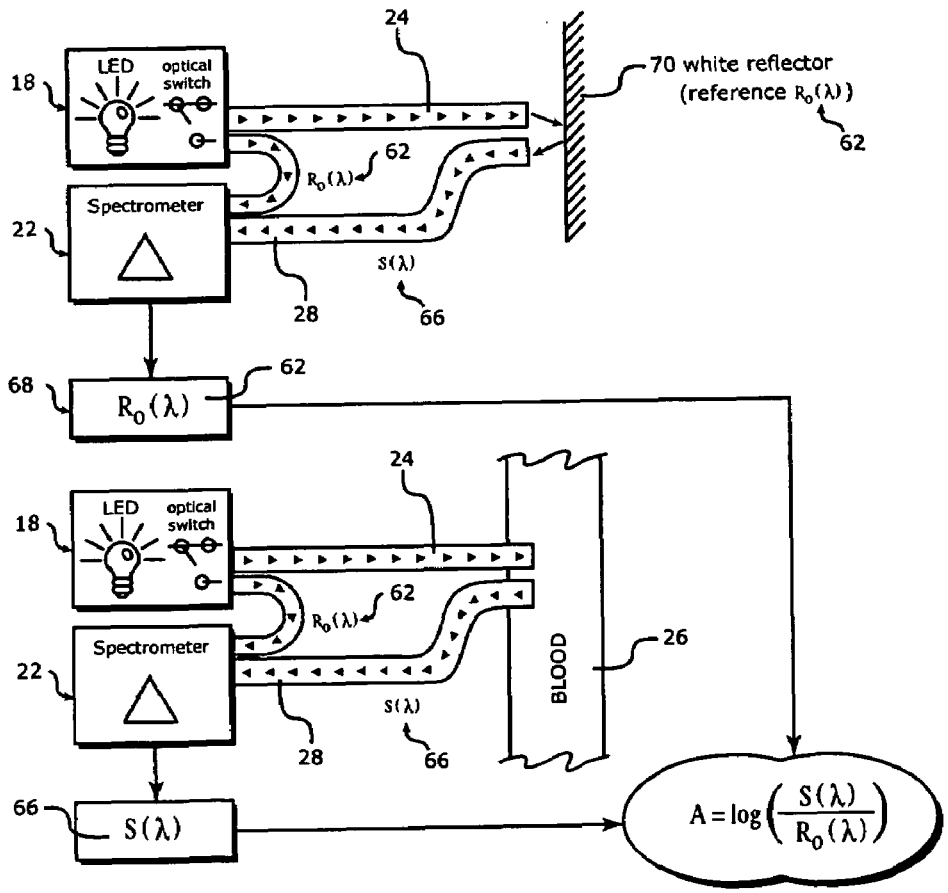
FIG. 6 is another schematic representation of step 36 of FIG. 4.

Referring to FIG. 6, an alternate or additional method of determining tHb by measuring a reference signal is described. This method may include measuring the light source 18 and storing a reference spectrum signal $R_0(\lambda)$ 62 in memory 68 for later use. The light source communicates light through a transmit fiber 24 against a white reflector 70 in order to reflect a reference signal $R_0(\lambda)$ 62 back through the receive fiber 28 to the spectrometer 22 for storage in the memory 68. The reference spectra 62 is later recalled when a measurement of whole blood is made. For example, during a measurement of tHb in whole blood, the light source 18 transmits a light signal through the transmit fiber 24 to whole blood 26, and a return signal is transmitted through a receive fiber 28 to the spectrometer 22 to produce a signal $S(\lambda)$ 66. The signal $S(\lambda)$ 66 is then compared to the reference signal 62 using the logarithm previously described with reference to FIG. 5.

That is, absorptivity may be equal to the logarithm of signal 66 divided by the signal 62. The light source 18 used in the apparatus and method described with reference to FIG. 6 is generally spectrally stable. If the light source 18 spectra changes, an error will occur and a new reference spectra 62 may be made in order to provide accurate results. A white LED will likely produce the most spectral stability over time for this embodiment, for reasons including those previously discussed.

Figure 7:
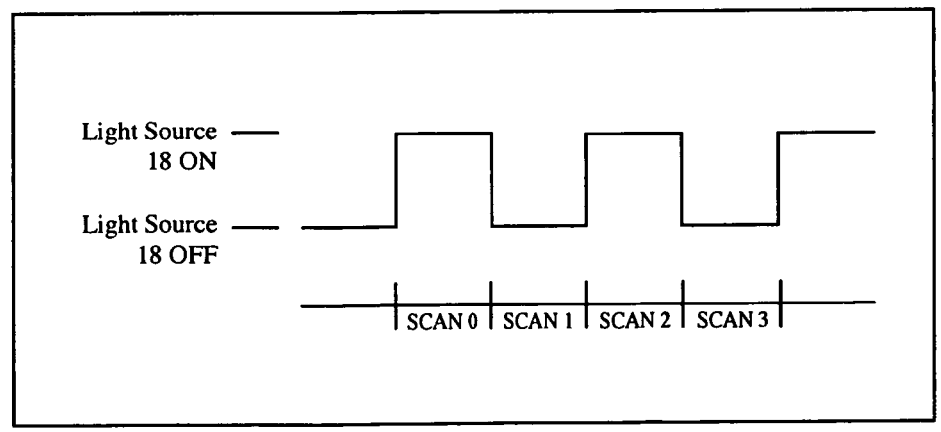
FIG. 7 is a timing diagram illustrating step 38 of FIG. 4.

Referring to FIG. 7, the step 38 of measuring a dark signal described with reference to FIG. 4 is illustrated and described in more detail. During step 38, the light source 18 is turned off in order to perform a measurement of the dark signal DK(λ). The purpose of measuring the dark signal while the light source is turned off is to provide a measurement of the signal change as a function of the thermal offset of the spectrometer 22 and any ambient light or other signals (electronic or optical) that may be present which interferes with the measurement of light absorbance when the light source is turned on. The dark signal DK(λ) includes all data that is measured when the light source 18 is turned off. The dark signal DK(λ) is subtracted from the signal measured with the light turned on. This step may be used to improve the accuracy of the results.

Thus, as shown in FIG. 7, the state of the LED or light source 18 may be both on and off. During scan 0, the LED is turned on. During scan 0, the spectrometer measures a light absorbance of tHb in blood plus thermal noise plus ambient light. Later, the light source 18 is turned off during scan 1. During scan 1, there is no measure of absorptivity or reflected light from the tHb within the blood. However, thermal noise and ambient light may still exist and may be measured during scan 1. The results of scan 1 may then be subtracted from the results of scan 2 to reduce any effects of thermal noise and ambient light and any other common mode noise that may interfere with the measurement from the results in order to yield only the results of measured absorbance of light by the tHb within the whole blood. This method described may be shown mathematically as follows:

Scan 0 = $I_{blood} + I_{thermal\ noise} + I_{ambient}$

Scan 1 = $I\cancel{/_{blood}}^{0} + I_{thermal\ noise} + I_{ambient}$ since LED = off Scan = Scan 0 - Scan 1

Scan = $(I_{blood} + I_{thermal\ noise} + I_{ambient}) - (I_{thermal} + I_{ambient})$ Scan = $I_{blood}$ Referring to FIG. 4, after steps 36 and 38 are performed, steps 40 through 48 are performed and are described in greater detail as follows. Step 40 turns the light source 18 on and measures the tHb dependent remitted spectra signal RM(λ) from the whole blood. After steps 40 and 42, the measured remitted spectra signal RM(λ) is checked or verified to ensure that the signal level of the remitted spectra signal RM(λ) is within a desired range. If the remitted spectra signal RM(λ) is out of range, the power to the light source 18 or the integration time may be adjusted at step 44. The integration time is the time the spectrometer needs to collect the desired signals which may later be adjusted at step 44. If an adjustment, at step 44, of the light source 18 or the integration time is made, then a new dark and remitted signal is made and rechecked at steps 38, 40, and 42.

At step 44, the undesired dark spectra is removed from the remitted signal by subtracting DK(λ) from RM(λ). The dark signal DK(λ) is subtracted, pixel-by-pixel, from the remitted spectra RM(λ). The result is a corrected remitted spectra without bias and without ambient interference. This process is described and illustrated with reference to FIG. 7. At steps 46 and 48, noise is removed from both the reference signal RF(λ) and the remitted signal RM(λ). One method to remove noise from both signals is to apply a moving average (MA) filter to the two spectral signals. Another method is to use a Savitsky-Golay filter, which is more efficient than the MA filter. The same filter should be applied to both signals in order to ensure consistency between both the reference and remitted spectral signals.

Figure 8:
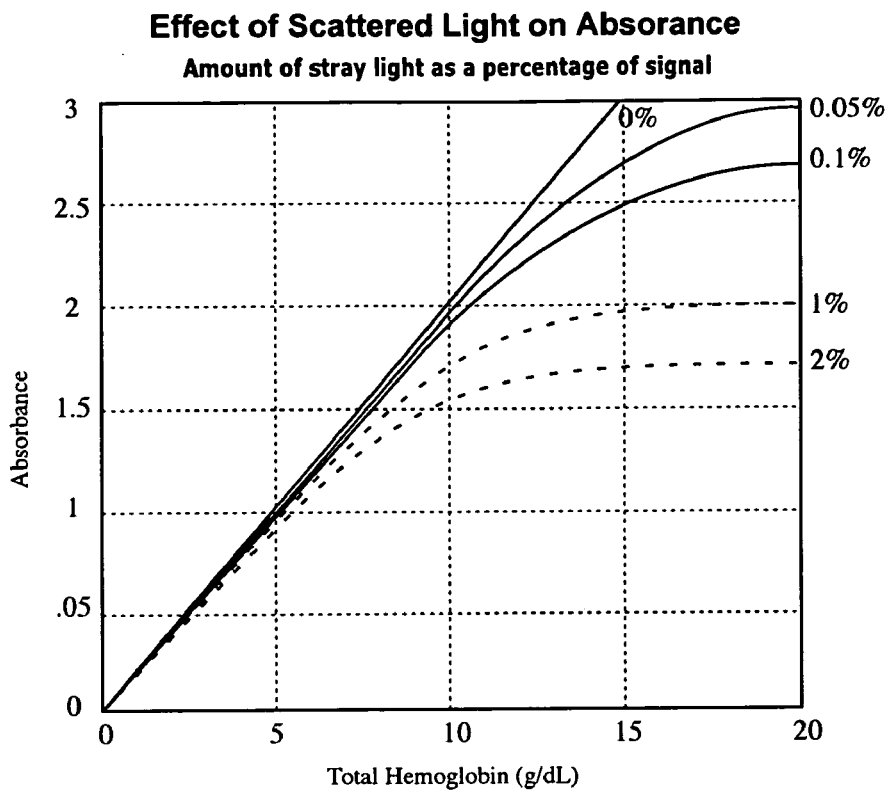
FIG. 8 is a chart illustrating the stray light results, as percentages, referred to in step 50 of FIG. 4.

Referring to FIG. 8, step 50 as described with reference to FIG. 4 is shown and described in more detail. At step 50, the method corrects for stray light within the spectrometer 22. Stray light affects the measurement of absorbance and tHb by reducing the affective absorbance change. Stray light exists in all spectrometers to varying degrees. The stray light present in a particular spectrometer 22 depends on the design and quality of the internal components within the spectrometer 22. The amount of stray light for any spectrometer must be determined empirically. The measured value of stray light for each spectrometer may then be used to correct the absorbance calculation. As shown in FIG. 8, the effect of different levels of stray light can be seen in a tHb/Hct analysis model. The Analysis model illustrates the nonlinear results that would be obtained from experimental data if an experiment were performed, showing an amount of stray light as a percentage of the signal, for example, ranging from about 0 percent to about 2 percent stray light.

Figure 9:
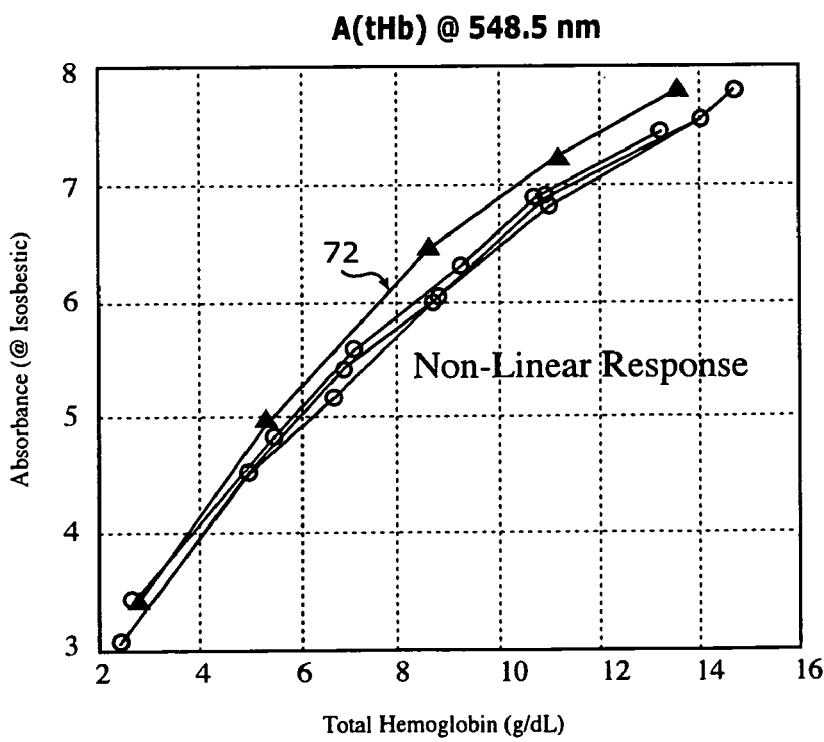
FIG. 9 is a chart illustrating actual experimental results shown in FIG. 8.

Referring to FIG. 9, the nonlinear results discussed with reference to FIG. 8 are shown as actual experimental results. The results reveal total absorbance of light by tHb at a wavelength of about 548.5 nm for four different spectrometers. Spectrometers such as those manufactured by Ocean Optics or Avantes may be used to produce similar results. The spectrometer providing the results of the slope 72 yielding the highest absorbance values illustrates a 0.05 percent amount of stray light as a percentage of the absorbance signal. All other slopes are shown grouped relatively close to each other.

Returning again to FIG. 4, step 52 calculates the absorbance from the corrected remitted signal and the reference signal. Absorbance may be calculated, for example, using the following formula:

$$A(\lambda) = \log\left(\frac{\text{remitted}(\lambda)}{\text{reference}(\lambda)}\right)$$

Step 54 calculates an n-point average about the wavelength 12 that is insensitive to tHb changes. Since absorbance is low at point 12 and point 12 is on the edge of the spectral output of the light source 18, reducing noise about this point 12 improves the accuracy of the total measurement.

Figure 10:
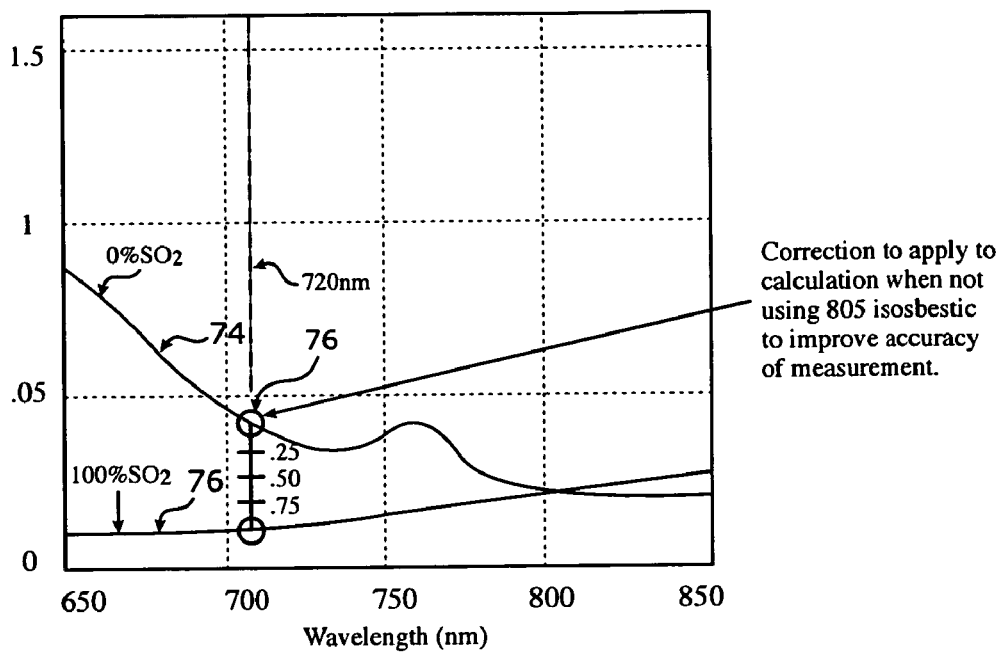
FIG. 10 is a chart illustrating correction for oxygen saturation according to step 56 of FIG. 4.

Referring to FIG. 10, step 56 of FIG. 4 is described in greater detail. Step 56 corrects for the absorbance error at point 12, for example about 720 nm, due to the effect of oxygen saturation. A shorter wavelength than a wavelength of about 805 nm may be used. Using a wavelength shorter than 805 nm is important where a white LED is used as the light source 18, since there is no spectral power providing helpful data at about 805 nm using a white LED. Thus, the spectral power approaches zero at about 750 nm as discussed with reference to FIG. 1. Therefore, a wavelength shorter than about 750 nm can be used, but such a wavelength may be sensitive to $SO_2$ changes. If $SO_2$ is known and the extinction coefficient of blood is known, one can apply an $SO_2$ dependent correction using the Lambert-Beer law. Thus, as shown in FIG. 10, a plot line of $SO_2$ at zero percent is shown as plot line 74 and a plot line illustrating $SO_2$ at one hundred percent is shown as plot line 76. A correction occurs by comparing plot line 74 to plot line 76, for example at a wavelength of about 720 nm. In order to provide such a comparison, $SO_2$ should be first calculated and known in order to apply an $SO_2$ dependent correction according to the Lambert-Beer law.

The apparatus may calculate the difference between the absorbance (dA) at the sensitive point 10 (at about 548 nm, for example) and the insensitive point 12 (at about 720 nm, for example) (Step 58 of FIG. 4). The formula for calculating the difference (dA) is A(548 nm)−A(720 nm), using example wavelengths of between about 548 nm and 720 nm.

Figure 11:
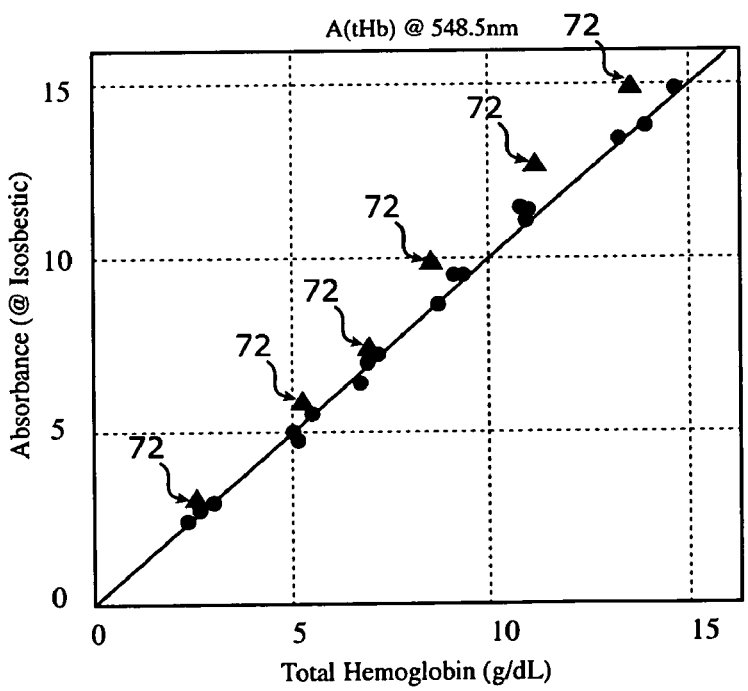
FIG. 11 is a chart illustrating empirical results of step 60 of FIG. 4.

Referring to FIG. 11, step 60 described with reference to FIG. 4 is described in greater detail. Step 60 applies a mathematical transform to convert the difference in absorbance (dA) to tHb. This function is empirically derived and is a function of the geometry of the catheter 20 used and of the optical properties of the spectrometer, such as stray light. An example of such a mathematical transform is a second order polynomial in the following form:

$$tHb=a(dA)^2+b(dA)+c$$

The purpose of this equation is to correct for the effect of stray light interference. As previously discussed with reference to FIGS. 8 and 9, the stray light effect of various spectrometers varies based on the specific spectrometer and/or spectrometer type used. For example, the plot points 72 illustrate the results of a first type of spectrometer; all other results are produced using various second types of spectrometers. Since each spectrometer has a different amount of stray light, the coefficients of the various spectrometers are unique to each spectrometer.

In an embodiment of a method for measuring tHb in whole blood, the difference of absorbance (dA) measured between at least two wavelengths may be performed using 805 nm as a point in the wavelength as a reference for the difference calculation. The 805 nm point does not change significantly with changes in tHB concentration as compared to the point 10.

In another embodiment, the difference between wavelengths may be calculated using a wavelength of about 720 nm. If the light source 18 is a white LED, its spectra contains no power above about 750 nm, as illustrated in the results of FIG. 1. This eliminates the need to use 805 nm as a wavelength. The 720 nm region can be used effectively, and to improve accuracy, if the oxygen saturation is known, then the absorbance at about 720 nm can be offset. The absorbance changes as a function of $SO_2$ and can be reasonably estimated as previously described using the extinction coefficience of blood at 720 nm.

Figure 12A:
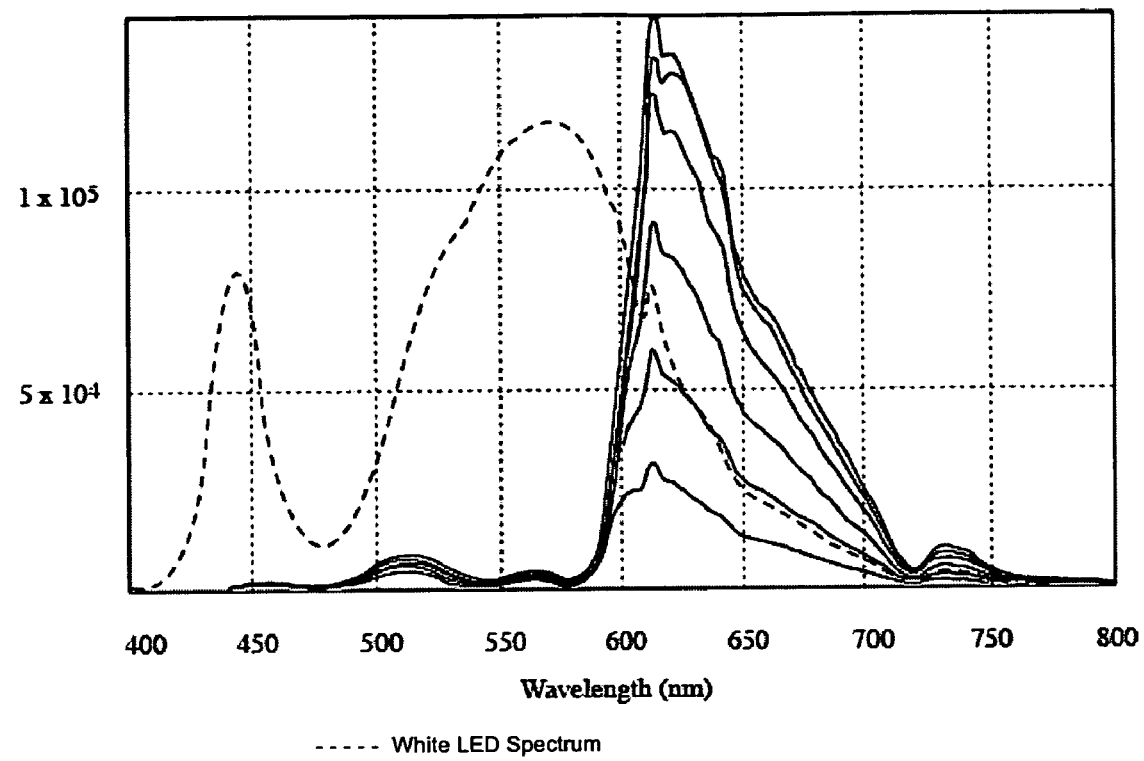
FIG. 12A is a transmission plot illustrating the spectral region where the remitted signal saturates the spectrometer during normal measurements.

Referring to FIG. 12A, a transmission plot illustrates the spectral region which contributes to stray light. When using a white LED and the remitted signal RM(λ) 40 is within the preferred range, the strong remitted signal from the bloodstream in the 600-700 nm region exceeds the measuring capability of the spectrometer. It is the signal in this region that is primarily responsible for the measurement errors due to stray light. The amount of stray light within the spectrometer is proportional to the total amount of light entering the spectrometer. Therefore, to estimate the stray light content, the peak signal intensity within the 600-700 nm region must be determined. A method is described to determine the peak signal intensity so that stray light may be estimated and corrected for.

Figure 12B:
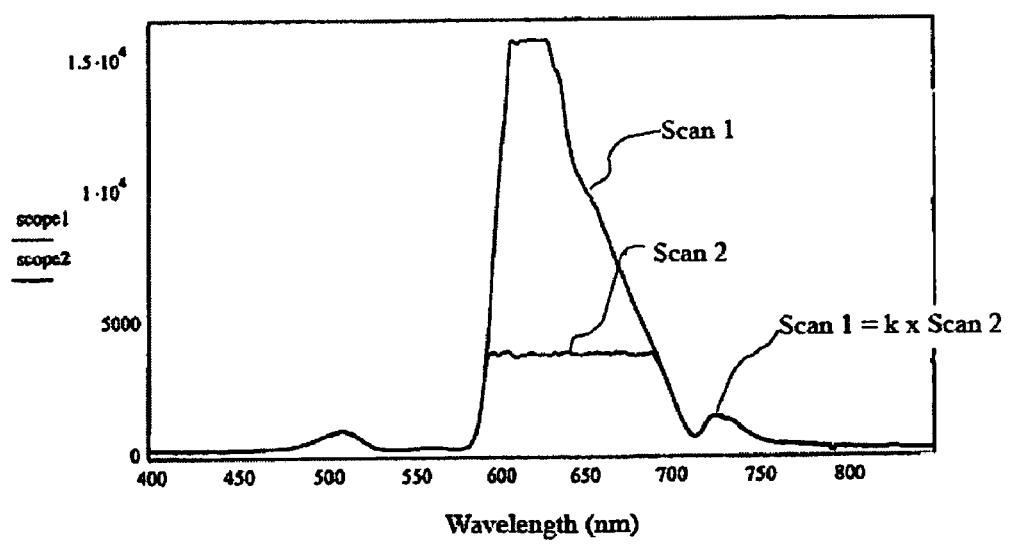
FIG. 12B is a transmission plot illustrating the spectral region used to estimate the stray light component.

Referring to FIG. 12B, a transmission plot illustrating the spectral region used to estimate the stray light component is shown. Scan 1 is measured at a low integration time or a low LED intensity. Scan 2 is measured at a normal integration time or a normal LED intensity. Scan 1 is made at an integration time that is short enough to ensure that the detector is not saturated in the 600-700 nm region, or the LED output has be reduced to achieve the same. The normal and reduced remitted spectra may be scaled such that Scan 1=k * Scan 2, where k is a scaling factor used to match the signal intensities in a non-saturated region such as in the 450-575 nm region or the 700-750 nm region. Once the scaling factor is determined that equates the two signals, the peak signal intensity can be determined for estimating the actual stray light in the measurement.

Figure 13:
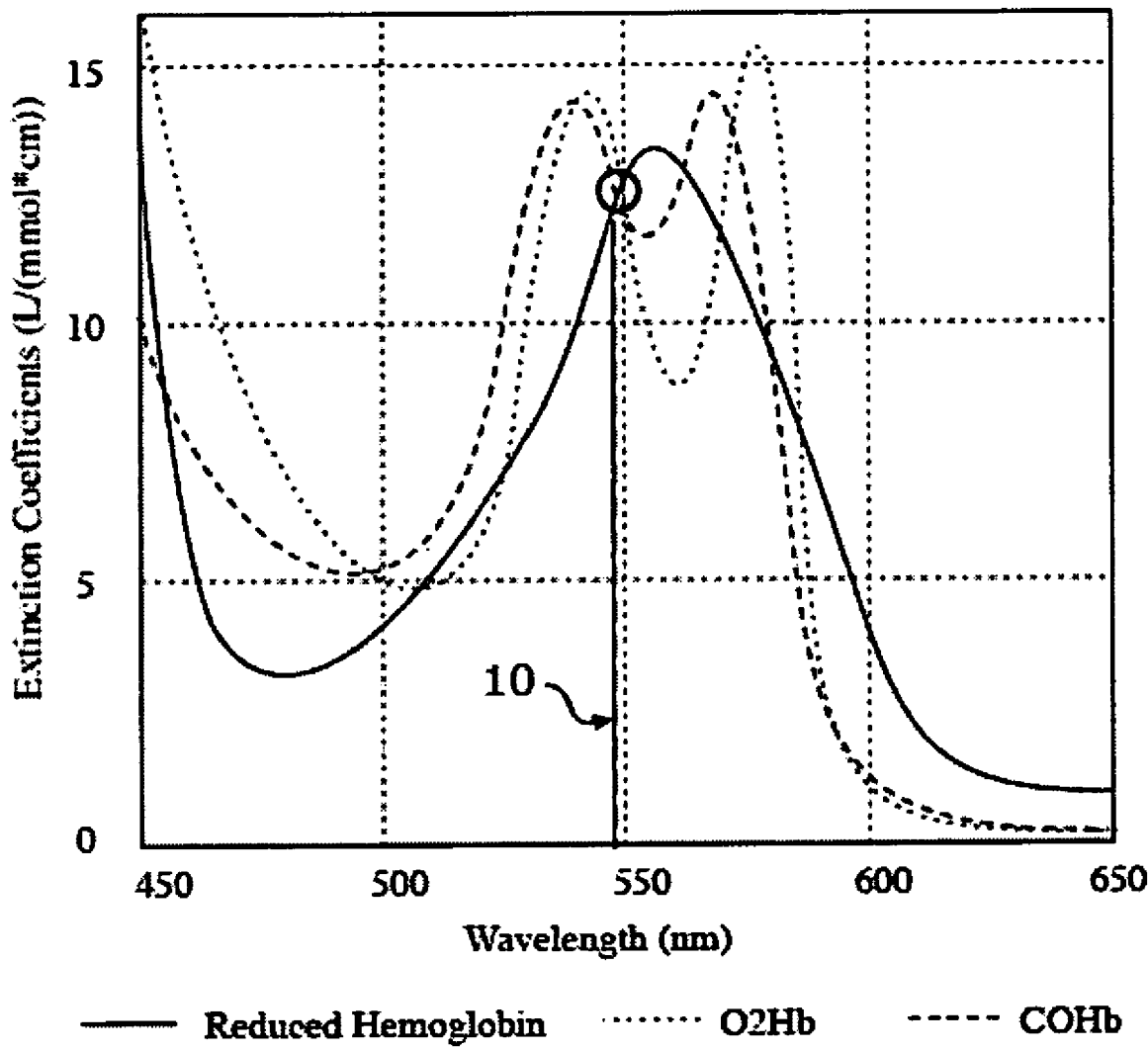
FIG. 13 is a chart illustrating advantages of a wavelength of about 548 nm.

Referring to FIG. 13, a method used to measure the tHb of whole blood is shown and described. In this embodiment, about 548 nm may be used as a point 10. The point 10 at about 548 nm is a triple isosbestic point that is independent of both oxyhemoglobin ($O_2Hb$) and carboxyhemoglobin (COHb).

The various systems and methods described above have been tried experimentally. The results are now described in order to illustrate and demonstrate the use of the various methods and systems.

In a first experiment, many of the concepts described above were tried. In this experiment, bovine blood was circulated in an invitro blood loop. During the course of the experiment, the blood was diluted with an isotonic saline solution. At each dilution, the blood was measured using the configuration described above. Blood spectra was collected and analyzed over the spectral range from about 400 nm to about 850 nm.

The data was then analyzed in several ways. First, the data was analyzed by evaluating the relationship of absorbance at about 523 nm and at about 585 nm as wavelength points as a function of changes in tHb. A line was calculated that intersected the absorbance at the two wavelength points of about 523 nm and about 585 nm. The slope of the line was expected to change as a function of tHb.

Another experiment evaluated tHb using the absorbance difference (ΔA) between two spectral regions (Δλ). The two spectral regions include one region that is sensitive to tHb changes (ΔtHb) and another that is insensitive to ΔtHb. The spectral regions employed included the wavelength of about 548 nm as the sensitive region and the wavelength point of about 805 nm as the insensitive region to compare ΔtHb. However, the LED was not capable of delivering sufficient optical power at the point of about 805 nm to provide adequate measurements. Further, the spectrometer did not appear to include a measurable spectral range beyond about 720 nm.

Figure 14:
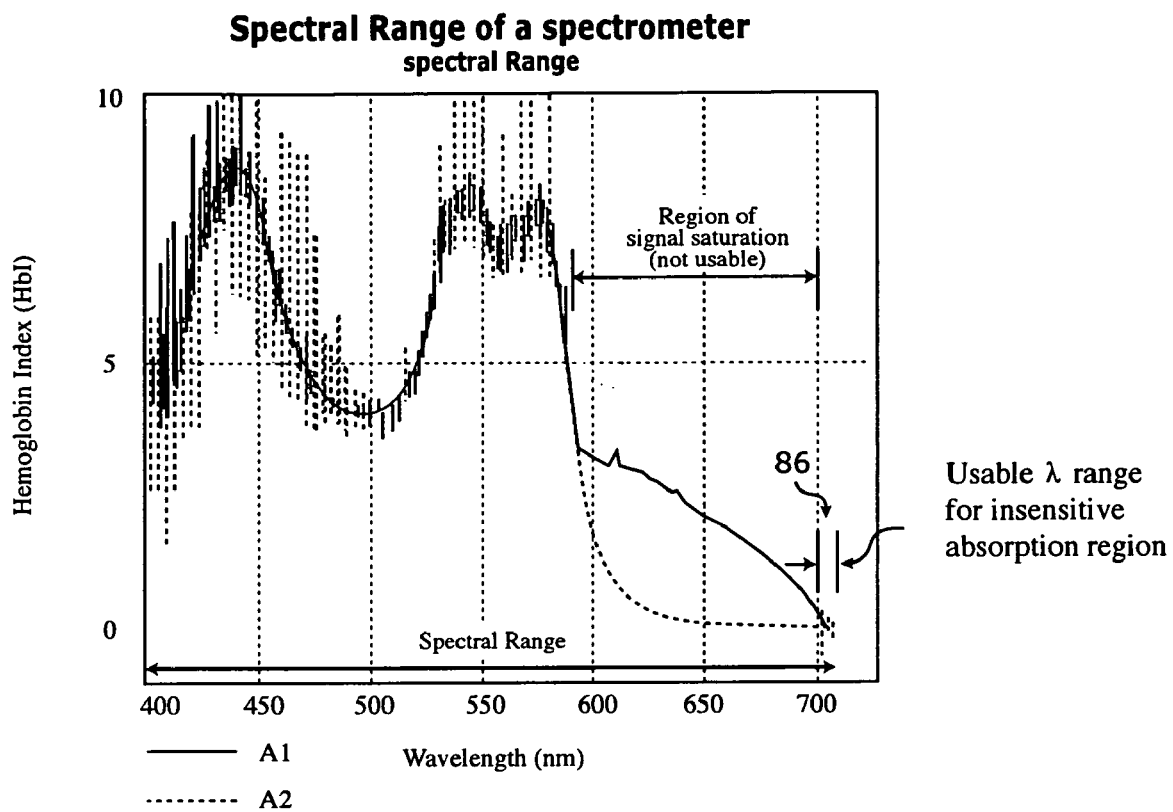
FIG. 14 is a chart illustrating a spectral range of a spectrometer that can be used to measure tHb.

Referring to FIG. 14, based on the range limitations discussed above, the longest measurable wavelength was approximately 720 nm. The point of 720 nm was thus used as the insensitive region. While this region is still sensitive to oxygen saturation changes, the difference between light absorbance at about 700-750 nm and at about 500 nm was small enough to prevent any significant errors in calculation. The region of about 700-750 nm was also a region that did not appear to saturate at different integration times. The usable range 86 for the insensitive absorbance region at about 700 nm is shown in FIG. 14.

Figure 15:
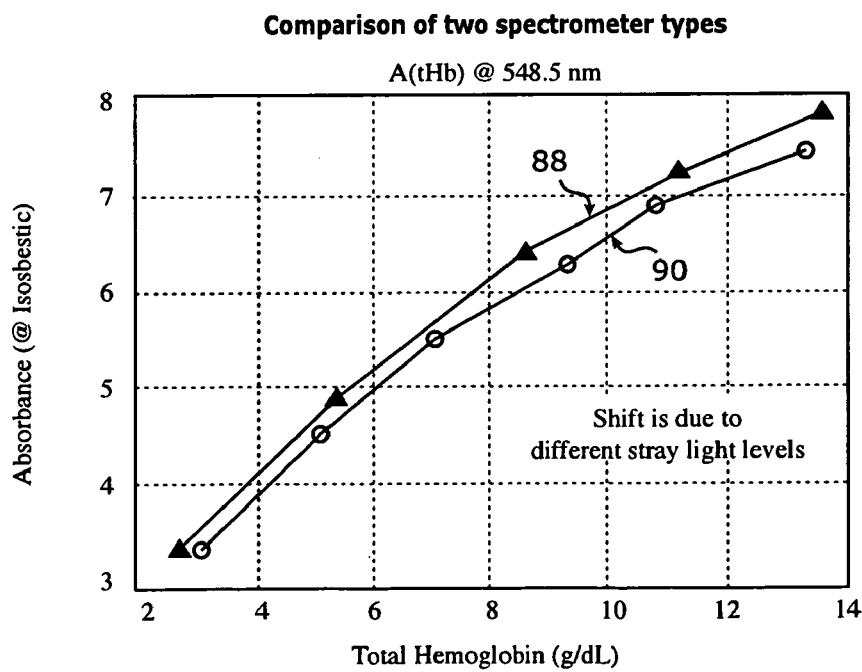
FIG. 15 is a chart illustrating a comparison in the absorbance and total hemoglobin for two spectrometers.

Referring to FIG. 15, the results indicate that there is a well-behaved relationship between the first 88 and the second 90 spectrometer system types regarding tHb and ΔA. There was a slight difference in the response of both the systems 88 and 90, but both systems responded in a linear-like manner. These results revealed that the measurement of tHb using the methods discussed above is feasible and relatively independent of the type of spectrometer 22 used.

The non-linearity illustrated in FIGS. 8, 9, 11 and 16 may be explained by the stray light distortion of the specific spectrometers used. Stray light inside the spectrometers distorts the absorbance measurement as described previously. Correcting for stray light using the steps described in the methods above should improve the linearity of ΔA as tHb changes or as a function of tHb changes. The polynomial equation described with reference to step 60 is unique to each spectrometer and/or spectrometer type 22.

Figure 16:
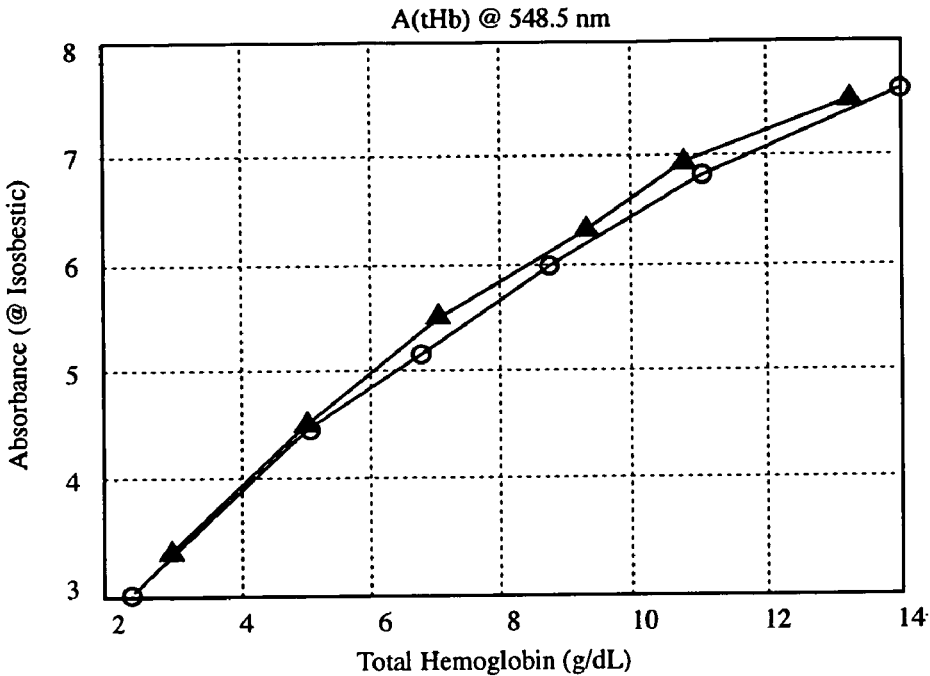
FIG. 16 is a chart comparing stable oxygen saturation with variable oxygen saturation, showing oxygen saturation independent of measurement technique.

Referring to FIG. 16, another experiment similar to the experiment described above was performed in order to evaluate the dependency of the results upon oxygen saturation. Oxygen saturation was changed randomly in order to evaluate the variation of changes in oxygen saturation on the tHb measurement. The results of this experiment are 'shown in FIG. 16 As shown in FIG. 16, a stable oxygen saturation 92 yielded very similar results to oxygen saturation 94 that was changed randomly. The results show no significant dependency upon variable oxygen saturation. These results support the use of a non-isosbestic wavelength as the reference wavelength in the absorbance difference equation.

Figure 17:
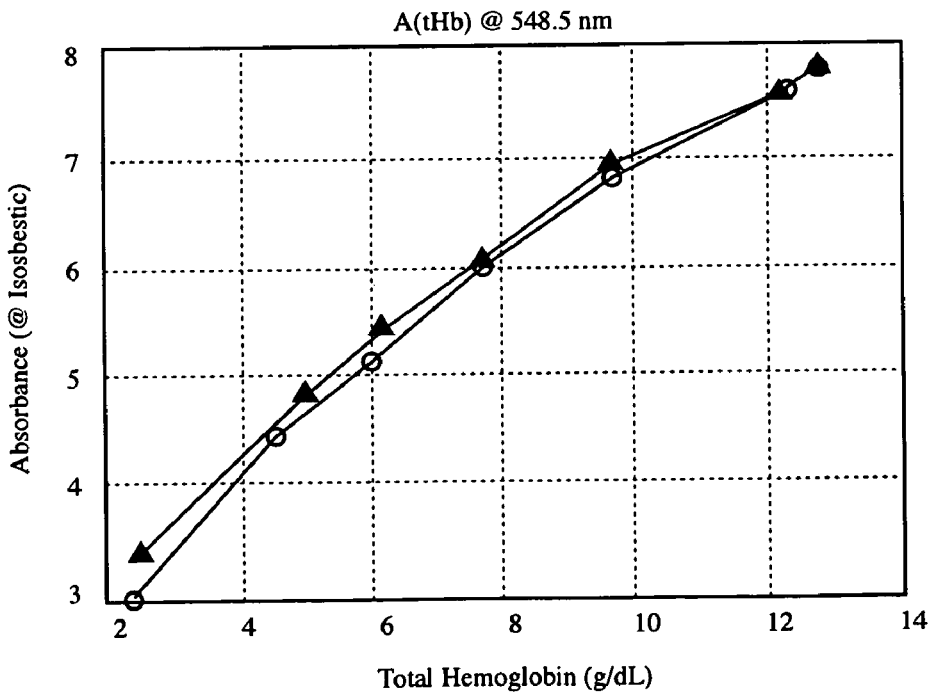
FIG. 17 is a chart illustrating the effect at different levels of scattering on total hemoglobin measurement.

Yet another experiment was conducted in order to evaluate the different amounts of scattering on tHb. The experiment was the same as the previous experiment with the exception that a different diluent was used to change tHb. In previous experiments, tHb was changed by adding plasma-lyte solution, which is a common crystalloid solution used as an intravascular volume expander. The present experiment, by contrast, diluted with blood plasma. Scattering is dependent upon the refractive index (RI) difference between the red blood cell and the solution containing the red blood cell. The RI of the blood cell is about 1.41, the RI of plasma is about 1.38, and the RI of plasmalyte is 1.33. Using plasma-lyte as the diluent increased the overall scattered signal, while diluting with plasma reduced scattering. The results, as shown in FIG. 17, reveal that there is no significant difference in the measurement of tHb as a result of different amounts of scattering using various diluents having different refractive indexes.

An example of a computer algorithm that may be used to estimate the peak intensity for stray light correction according to the systems and methods discussed above is as follows:

$$S \leftarrow medsmooth(\text{remit}, 11)$$

$$[\min \leftarrow \text{floor}(0.995 \cdot \max(S))$$

$$\text{for } px \in 2 \ldots \text{rows}(S) - 2$$

$$PXlo \leftarrow px \text{ if } (S_{px+1} > lmin) \wedge (S_{px-1} < lmin)$$
$$PXhi \leftarrow px \text{ if } (S_{px-1} > lmin) \wedge (S_{px+1} < lmin)$$

$$\Delta\lambda \leftarrow \lambda_{PXhi} - \lambda_{PXlo}$$

$$SPeak \leftarrow \text{floor}\left(\frac{\max(S)}{-0.0092 \cdot \Delta\lambda + 1}\right)$$

$$StrayLight \leftarrow SL \cdot SPeak.$$

An example of a computer algorithm used to calculate tHb from absorbance data according to the systems and methods discussed above is as follows:

$$Hgb1\lambda \leftarrow 548.5$$

$$Hgb2\lambda \leftarrow 704.0$$

$$BXWin \leftarrow 10$$

$$MDWin \leftarrow 11$$

$$\text{remit} \leftarrow \text{boxcar}(medsmooth(\text{remit}, MDWin), BXWin) - StrayLight$$

$$\text{dark} \leftarrow \text{boxcar}(medsmooth(\text{dark}, MDWin), BXWin)$$

$$\text{white} \leftarrow \text{boxcar}(medsmooth(\text{white}, MDWin), BXWin)$$

$$NoOfPixels \leftarrow \text{length}(\text{remit})$$

$$\text{for } i \in 0 \ldots NoOfPixels - 2$$

$$\text{"Find } HgbPixels\text{"}$$
$$Hgb1Pix \leftarrow i \text{ if } \lambda_i < Hgb1\lambda$$
$$Hgb2Pix \leftarrow i + 1 \text{ if } \lambda_i < Hgb2\lambda$$

$$\text{if } (\text{remit}_{Hgb2Pix} > \text{dark}_{Hgb2Pix}) \wedge (\text{white}_{Hgb2Pix} > 0)$$
$$\quad \text{"Check 704 nm for valid numbers"}$$
$$\quad A2 \leftarrow -\log\left(\frac{\text{remit}_{Hgb2Pix} - \text{dark}_{Hgb2Pix}}{\text{white}_{Hgb2Pix}}\right)$$
$$\quad \text{if } (\text{remit}_{Hgb1Pix} > \text{dark}_{Hgb1Pix}) \wedge (\text{white}_{Hgb1Pix} > 0)$$
$$\quad\quad \text{"Check 548 nm for valid numbers"}$$
$$\quad\quad A1 \leftarrow -\log\left(\frac{\text{remit}_{Hgb1Pix} - \text{dark}_{Hgb1Pix}}{\text{white}_{Hgb1Pix}}\right)$$
$$\quad\quad \Delta A \leftarrow A1 - A2$$
$$\quad\quad HGB \leftarrow 1.784 - 1.1189 \cdot (\Delta A) + 1.5336 \cdot (\Delta A^2)$$
$$\text{otherwise}$$
$$\quad \Delta A \leftarrow 0$$
$$\quad HGB \leftarrow 0$$
$$HGB$$

As mentioned throughout this specification, the devices, systems, and methods described herein provide various advantages. One of these advantages provides a method of employing only two single wavelength points within the visible light range. Thus, measurement within the infrared light range is unnecessary. A catheter may employ fiber optics that would otherwise absorb the heat from infrared light.

Further, additional advantages provide that a spectrometer may measure many more than two points along the visible spectrum. Further still, any number of additional measurements may be employed in addition to the measurements provided according to the methods described above. For example, oxyhemoglobin, carboxyhemoglobin, and other forms and states of hemoglobin and other substances within whole blood may be measured in addition to the variables measured above. The data gathered from such measurements may be used in combination with the methods above in order to provide additional tuning, other adjustments, and/or information in order to provide more accurate, comprehensive and/or useful results. Such additional results may provide useful information to users and patients capable of improving the diagnosis and treatment of such patients.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method of determining total hemoglobin of whole blood to guide patient treatment, comprising:
   transmitting light at multiple wavelengths in the visible spectrum into whole blood;
   receiving the light from the whole blood;
   determining light absorbance of the light at each of the multiple wavelengths;
   determining a change in the light absorbance of the light between the multiple wavelengths; and
   determining total hemoglobin of the whole blood using the change in the light absorbance of the light between the multiple wavelengths in proportion to a difference between the wavelengths;
   providing the total hemoglobin for patient treatment.

2. The method of claim 1, wherein the multiple wavelength are between about 500 nanometers and about 900 nanometers.

3. The method of claim 1, wherein the multiple wavelengths include a first wavelength between about 500 nanometers and about 600 nanometers and a second wavelength between about 625 nanometers and about 850 nanometers.

4. The method of claim 1, wherein the multiple wavelengths include a first wavelength between about 500 nanometers and about 600 nanometers and a second wavelength between about 700 nanometers and about 720 nanometers.

5. The method of claim 1, wherein the multiple wavelengths include a first wavelength of about 548 nanometers and a second wavelength of about 805 nanometers.

6. The method of claim 1, wherein the first wavelength is between about 700 nanometers and about 720 nanometers.

7. The method of claim 1, wherein the second wavelength is between about 540 nanometers and about 560 nanometers.

8. The method of claim 1, wherein the multiple wavelengths include a first wavelength and a second wavelength where the first wavelength yields less change in the light absorbance than the second wavelength.

9. The method of claim further comprising relating the total hemoglobin of the whole blood to hematocrit.

10. A method of determining total hemoglobin of whole blood to guide patient treatment, comprising:
    providing a light source configured to emit light at multiple wavelengths;
    measuring a reference signal containing a spectra of the light source;
    measuring a dark signal when the light source is off;
    measuring a remitted signal from whole blood when the light source is on;
    determining light absorbance from the reference signal and the remitted signal; and
    determining total hemoglobin of the whole blood based on a change in the light absorbance between the multiple wavelengths in proportion to a difference between the wavelengths;
    providing the total hemoglobin for patient treatment.

11. The method of claim 10, further comprising removing noise from the reference signal and the remitted signal prior to determining light absorbance from the reference signal and the remitted signal.

12. The method of claim 10, further comprising:
    verifying that the remitted signal is within a preferred range; and
    removing dark spectra from the remitted signal.

13. The method of claim 10, further comprising correcting for stray light from the light source.

14. The method of claim 10, further comprising calculating an n-point average about at least one of the multiple wavelengths.

15. The method of claim 14, further comprising correcting for light absorbance error of the at least one of the multiple wavelengths due to the effect of oxygen saturation.

* * * * *